United States Patent
Hiltawsky et al.

(10) Patent No.: US 8,100,831 B2
(45) Date of Patent: Jan. 24, 2012

(54) DIRECT STRAIN ESTIMATOR FOR MEASURING ELASTIC PROPERTIES OF TISSUE

(75) Inventors: Karsten Hiltawsky, Garching b. Munchen (DE); Christopher R. Hazard, Niskayuna, NY (US); Feng Lin, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 1062 days.

(21) Appl. No.: 11/562,920

(22) Filed: Nov. 22, 2006

(65) Prior Publication Data

US 2008/0119732 A1 May 22, 2008

(51) Int. Cl.
*A61B 8/00* (2006.01)

(52) U.S. Cl. ........ 600/438; 600/407; 600/442; 600/443; 600/447

(58) Field of Classification Search .................. 600/437, 600/438, 442, 443, 449
See application file for complete search history.

(56) References Cited

U.S. PATENT DOCUMENTS

| | | | |
|---|---|---|---|
| 5,178,147 A | 1/1993 | Ophir et al. | |
| 6,099,471 A * | 8/2000 | Torp et al. | 600/438 |
| 6,508,768 B1 | 1/2003 | Hall et al. | |
| 6,520,913 B1 | 2/2003 | Pesavento et al. | |
| 7,107,159 B2 * | 9/2006 | German | 702/41 |

FOREIGN PATENT DOCUMENTS

| | | |
|---|---|---|
| WO | 2006/005632 A1 | 1/2006 |
| WO | 2006/026552 A1 | 3/2006 |

OTHER PUBLICATIONS

J. Fromageu et al., "Description of a New Strain and Displacement Estimator for Elastography," IEEE Ultrasonic Symposium, 2003, pp. 1911-1914.
E. Brusseau et al., "Axial Strain Imaging Using a Local Estimation of the Scaling Factor from RF Ultrasound Signals," Ultrasonic Imaging 22, 2000, pp. 95-107.
M. O'Donnell et al., "Internal Displacement and Strain Imaging Using Ultrasonic Speckle Tracking," IEEE TUFFC, vol. 41, 1994, pp. 314-325.
A. Pesavento, "A Time Efficient and Accurate Strain Estimation Concept for Ultrasonic Elastography Using Iterative Phase Zero Estimation," IEEE TUFFC, vol. 46(5), 1999, pp. 1057-1067.
S. Srinivasan et al., "A Zero-Crossing Strain Estimator for Elastography," Ultrasound in Med. & Biol. 29(2), 2003, pp. 227-238.

(Continued)

*Primary Examiner* — Tse Chen
*Assistant Examiner* — Mark Remaly
(74) *Attorney, Agent, or Firm* — Seema Katragadda (57) ABSTRACT

Ultrasound data of a biological tissue is acquired in a relaxed state and a tensed state. A strain is estimated directly from the relaxed state ultrasound data and the tensed state ultrasound data by way of an imaginary part of a complex correlation function. In estimating the strain, the tensed state ultrasound data is re-stretched, and the imaginary part of the complex correlation function is calculated from this re-stretched ultrasound data and the relaxed state ultrasound data. A slope factor is also calculated, and the strain is estimated from this slope factor and the imaginary part of the complex correlation function.

27 Claims, 2 Drawing Sheets

OTHER PUBLICATIONS

W.F. Walker et al., "A Fundamental Limit on Delay Estimation Using Partially Correlated Speckle Signals," IEEE TUFFC, vol. 42(2), 1995, pp. 301-308.

Y. Zhu et al., "A Modified Block Matching Method for Real-Time Freehand Strain Imaging," Ultrasonic Imaging, vol. 24, May 2002, pp. 161-176.

S.K. Alam et al., "An Adaptive Strain Estimator for Elastography," IEEE TUFFC, vol. 45(2), 1998, pp. 461-472.

J. Fromageau et al., "Characterization of PVA Cryogel for Intravascular Ultrasound Elasticity Imaging," IEEE TUFFC, vol. 50(10), 2003, pp. 1318-1324.

* cited by examiner

DIRECT STRAIN ESTIMATOR FOR MEASURING ELASTIC PROPERTIES OF TISSUE

BACKGROUND OF THE INVENTION

The present invention relates generally to the use of ultrasound to study soft biological tissue and, more particularly, to the measurement of elastic properties of the tissue.

Determining the mechanical properties of biological tissue (e.g. parameters of elasticity) is of fundamental interest in clinical diagnosis because of the correlation between the healthy or pathological state of a tissue and its stiffness. It is known that some cancers are stiffer than normal tissues. This is the basis for hand palpitation used by physicians to diagnosis these disorders as well as self breast and testicular examinations. Beyond these more rudimentary techniques, imaging modalities capable of determining the relative stiffness of various tissues can also be very beneficial to cancer diagnosis in soft biological tissue. Numerous researchers have studied this field and there are a wealth of techniques in research and a few now in practice.

In recent years, ultrasound has been used to detect spatial variations in the elastic properties of biological tissue. This capability has led to a new imaging technique known as elastography. In elastography, the most common idea is to take images of tissue at two distinct levels of mechanical compression. The data from the two compression levels are compared to determine the local strain. Under well-controlled circumstances it is even possible to calculate the modulus of elasticity given this strain field, the boundary conditions and the applied stress. However, rarely is such a controlled environment attainable and thus the strain itself is used as a surrogate for the stiffness. Strain placed on the tissue associated with the compression is then measured by evaluating the variations within the ultrasound data induced by the stress, the idea being that large strains occur for softer tissues and smaller strains for harder tissues.

It is important to estimate strains with high accuracy in elastography since clinicians' diagnoses will be directly related to those estimations. This requires a processing that fits the local variations of the strain. Traditional strain estimation has been based on tracking the relative displacement of small windows of data from one frame to another under the two different compressive loads. The strain is then estimated as the spatial derivative of this displacement. Much work has gone into the study of this type of strain imaging. One of the problems with this type of strain estimation is that it does not account for the fact that locally the signals are compressed not just shifted. So as the level of strain increases, the ability to align the signals is reduced due to de-correlation of the signals. Thus, although this technique performs well for very small deformations (0.25%-1%), it fails rapidly with increasing strain. This is because, with the physical compression of the tissue, the signal is subjected to a variation in shape which is responsible for the decorrelation noise. One known technique stretches the post-compression signal temporally by the appropriate factor prior to time delay estimation. This preprocessing has been shown to improve the correlation between the pre- and postcompression signals and it compensates for the effect of compression at low strains. However, two fundamental limits arise: first, a prior knowledge of the strain magnitude is required; second, the proper temporal stretching factor depends on the local strain and cannot be constant over the signal.

Because of these limitations associated with time delay and displacement estimation techniques, techniques have been employed that estimate strain directly from the estimation of local scaling factors. Direct strain estimators estimate the local compression or stretching of the signals and thereby get the strain directly. These algorithms are capable of dealing with higher strain levels before de-correlation prevents estimation, such as strains greater than 1%.

While these techniques are an improvement over previous time delay estimation techniques, there still is a need for improving the accuracy of the measured strain, reducing the standard deviation of the measured strain, and increasing the efficiency with which these calculations can be carried out so as to make the process real-time capable. Direct strain estimation techniques that incorporate the imaginary part of the complex correlation function when estimating strain of the ultrasound data before and after compression would further improve these areas of need.

Still further improvements can be made on existing direct strain estimation techniques. Direct strain estimations are made on a window-by-window basis, thus the relative location of the windows used is determined in part by previously estimated values of the strain. This means that errors that occur in the strain estimation can accumulate or can in some cases completely destroy all the subsequent estimations. That is, if the strain estimation value is wrong, it can move the window to an extent that corresponding data from two adjacent windows does not substantially overlap. In these cases, the subsequent estimates of the strain will also be wrong. This shows up as vertical streaks of bad estimation in a strain display. Correcting the value used for the window location is very important to avoid these large lines of bad data. Thus, a strain estimation technique that can incorporate thresholds to filter out bad strain estimates, prospectively identify possible incorrect strain estimates before processing, and normalize strain data to reduce the biasing effect of incorrect strain estimates, would result in improved strain measurements.

It would therefore be desirable to have a method and a system that estimates strain directly from the imaginary part of the complex correlation function between two ultrasound data sets before and after compression and that further filters and normalizes strain data to minimize the impact of incorrect strain estimates.

SUMMARY OF THE INVENTION

The present invention is directed to a method, apparatus, and computer readable storage medium having a computer program thereon, the technical effect of which is to directly estimating strain in elastic tissue that overcomes the aforementioned drawbacks. Ultrasound data is analyzed before and after stressing by way of an iterative algorithm that estimates strain from the imaginary part of the complex correlation function.

Therefore, in accordance with one aspect of the present invention, an ultrasound system includes an ultrasound device configured to acquire a pair of ultrasound data sets from a biological tissue, wherein the pair of ultrasound data sets comprising acquired ultrasound data of the biological tissue in a relaxed state and in a tensed state. The system further includes a computer programmed to re-stretch the tensed state ultrasound data set, calculate an imaginary part of a complex correlation function between the relaxed state ultrasound data set and the re-stretched tensed state ultrasound data set, calculate a slope factor, and estimate a strain of the biological tissue from a relationship between the calculated imaginary part and the slope factor.

In accordance with another aspect of the present invention, a method of determining strain in an elastic tissue includes the steps of accessing a first set of ultrasound data acquired from the elastic tissue in an unstressed state and accessing a second set of ultrasound data acquired from the elastic tissue in a stressed state. The method further includes the steps of estimating a local strain of the elastic tissue based on an imaginary part of a complex correlation function between the first and second data sets and calculating a pre-delay for a subsequent correlation window based on the estimated local strain.

In accordance with yet another aspect of the present invention, a computer readable storage medium includes a computer program to adaptively control an ultrasound system for measuring strain in elastic tissue, the computer program representing a set of instructions that when executed by a computer causes the computer to analyze ultrasound data acquired from the elastic tissue between a stressed state and an unstressed state and estimate a local strain of the elastic tissue by performing an iterative calculation, wherein the local strain is proportional to an imaginary part of a complex correlation function of the acquired ultrasound data between the stressed state and the unstressed state. The computer program further causes the computer to calculate a pre-delay for a subsequent correlation window based on the estimated local strain.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE INVENTION

The present invention is directed to a method and apparatus for acquiring ultrasound data and using this data to perform elastography on biological tissue. The ultrasound data is analyzed between a relaxed state and a tensed state to estimate strain directly from the imaginary part of the complex correlation function of the ultrasound data.

Figure 1:
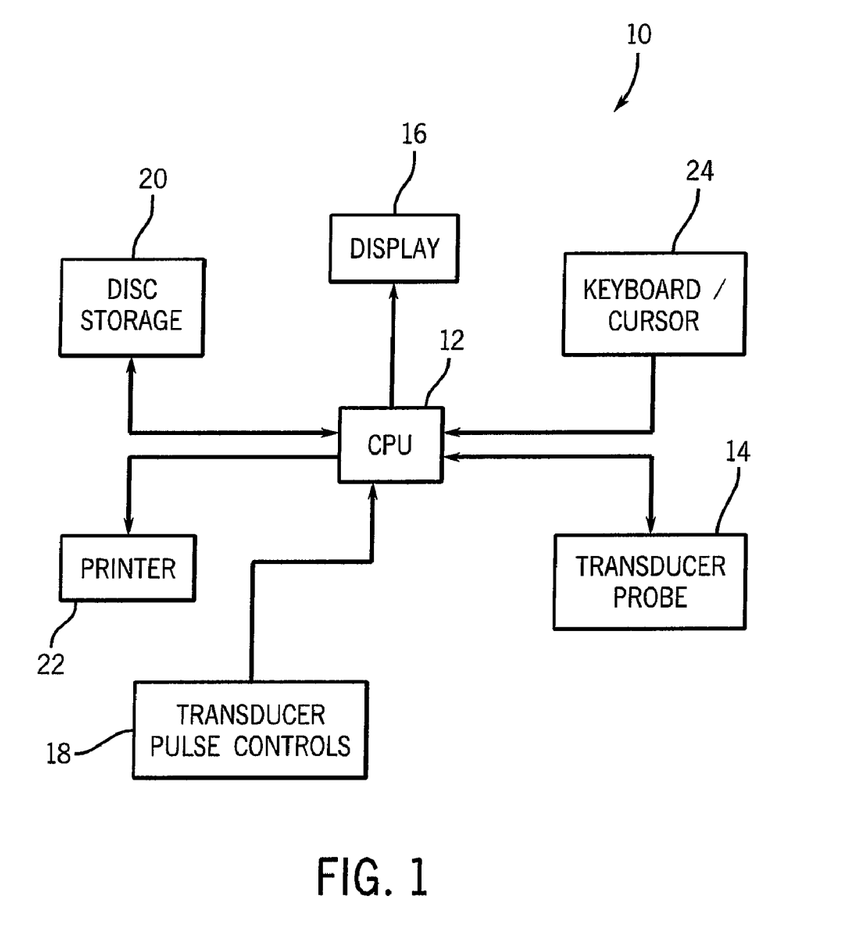
FIG. 1 is a schematic of an ultrasound system according to the present invention.

FIG. 1 illustrates a schematic diagram of an ultrasound imaging system 10 incorporating the present invention. The ultrasound system or machine 10 includes a computer (i.e., central processing unit) 12 that is operationally connected to a transducer probe 14 that generates and receives ultrasonic sound waves. In accordance with conventional construction, the transducer probe generates and receives sound waves using piezoelectric crystals, cMUTs, pMUTs, PVDF, single crystal or another material known in the art that, when energized by an electric current, change shape rapidly so as to produce sound waves that travel outwardly to an object to be imaged. Conversely, when sound or pressure waves hit the piezoelectric crystals, the crystals emit electrical currents that can be processed by the computer and reconstructed to form an image that is displayed on computer monitor or display 16. Ultrasound system 10 further includes transducer pulse controls 18 that allow the operator to set and change the frequency and duration of the ultrasound pulses as well as the scan mode of the ultrasound machine. The commands from the operator are translated into changing electric currents that are applied to the transducer piezoelectric elements.

Computer 12 sends electrical currents to the transducer probe to emit sound waves and also receives the electrical pulses from the probes that were created from the returning echoes. The computer also performs the necessary calculations involved in the processing of the received data for image reconstruction as well as other measurements that are carried out. Once the raw data is processed, the computer forms the image on monitor 16. The computer may also store the processed data and/or image on a disc 20 or cause a copy of the image to be printed on printer 22. Computer 12 also communicates with a keyboard/cursor which operates as an input device to allow the operator to add notes and to take measurements from the data.

As will be described in greater detail below, computer 12 of ultrasound system 10 is further configured to analyze the acquired ultrasound data for purposes of elastography. That is, computer 12 analyzes ultrasound data received from a biological, elastic tissue at an unstressed and a stressed state to determine strain. Monitor 16 can display maps of the estimated strain, or additionally, such maps can be printed on printer 22 and/or stored on disc 20.

Figure 2:
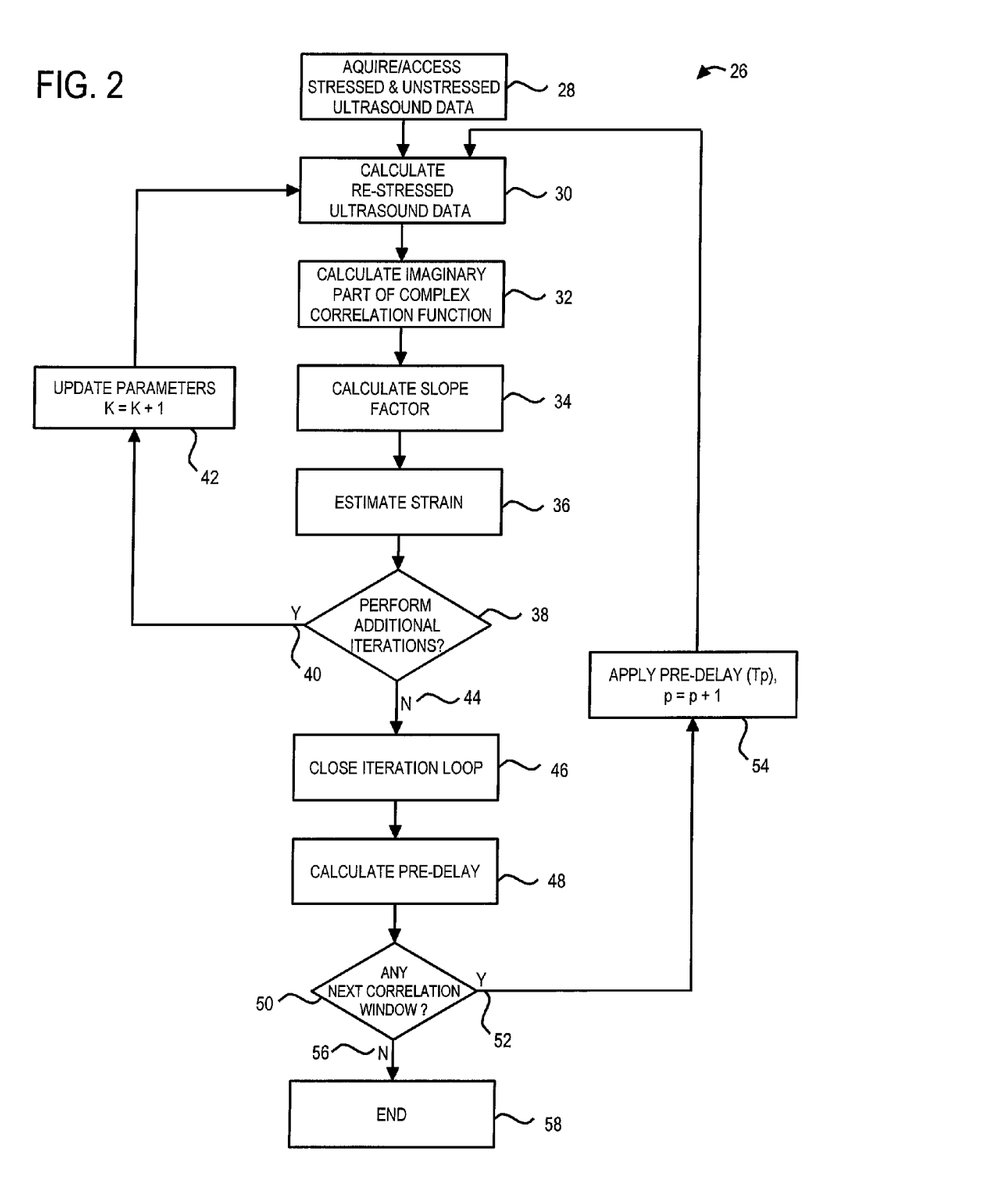
FIG. 2 is a flowchart setting forth the process of direct strain estimation of the present invention.

Referring now to FIG. 2, in a preferred embodiment, computer 12 is programmed to carry out a direct strain estimation technique 26 in performing the elastography from data acquired by ultrasound system 10 during an ultrasound scanning process. It is contemplated, however, that a stand-alone computer (not shown) having appropriate processing power may also carry out the direct strain estimation technique 26 separate from the process of acquiring the ultrasound data. The technique 26 begins by accessing 28 a first and second set of ultrasound data. The first and second sets of ultrasound data are acquired from the elastic tissue at an unstressed state and a stressed state. That is, data is acquired from the tissue when it is in a relaxed mode and in a tensed mode. Preferably, the tissue is mechanically compressed by an external force in the tensed mode; however, it is also envisioned that the tissue can be stretched as well.

From the ultrasound data, correlation windows are selected that represent ultrasound data acquired from the elastic tissue at reciprocal pre-stress and post-stress states. For each correlation window, the computer 12 iteratively estimates a local strain of the elastic tissue directly from the imaginary part of the complex correlation function between the unstressed data, r(t), and stressed data, s(t), as described below. For broadband ultrasound data, the unstressed data can be approximated as:

$$r(t)=A(t)\cos(\omega_0 t) \qquad \text{[Eqn. 1]},$$

where A(t) is the broadband envelop and $\omega_0$ is the center frequency of the signal, respectively, and upon introduction of compression or stretching, the stressed data can be expressed by a factor of $\epsilon$ and defined as:

$$s(t) = r(t \cdot (1 - \varepsilon)), \qquad \text{[Eqn. 2]}$$

or $$s(t) - A(t(1-\varepsilon))\cos(\omega_0 t(1-\varepsilon)). \qquad \text{[Eqn. 3]}$$

The strain estimation is comprised of a series of calculative steps that form an iterative algorithm loop, with the goal being to make the stressed signal, s(t) as similar as possible to the pre-stressed signal, r(t). The magnitude of the imaginary part of the complex correlation function is used as measure of how well the signals are matched. When the stressed signal is compressed with the appropriate strain value such that it is well matched to the pre-stressed signal, the imaginary part of the complex correlation function is zero. Thus the iterative algorithm can make use of this fact to converge on an answer. Further, it can be shown that the imaginary part of the complex correlation function is a linear function of the strain in the region near the correct answer. This linear functional form can be used to quickly converge in the iterative scheme.

In Eqn. 1, the pre-stressed signal was represented as a real signal. The analytic signal representation is given by $$\tilde{r}(t) = \frac{A(t)}{2} e^{i\omega_0 t},$$ [Eqn. 4]

wherein "~" stands for the analytical signal. A similar expression can be written for the analytic version of the stressed signal, $\tilde{s}(t)$. It can be shown that the uncompressed stressed signal $\tilde{u}(t)$ can be approximated as $$\tilde{u}(t) = \tilde{r}(t) e^{i\omega_0 t(\bar{\epsilon} - \epsilon)}$$ [Eqn 5], where $\bar{\epsilon}$ is the estimated strain value and $\epsilon$ is the actual strain value. Calculating the zero lag cross-correlation between $\tilde{r}(t)$ and $\tilde{u}(t)$ gives $$\int_{window} \tilde{r}(t) \tilde{u}^*(t) dt = \int_{window} \tilde{r}(t) \tilde{r}^*(t) e^{-i\omega_0 t(\bar{\epsilon} - \epsilon)} dt = \int_{window} \|\tilde{r}(t)\|^2 e^{-i\omega_0 t(\bar{\epsilon} - \epsilon)} dt$$ [Eqn 6].

This can be further approximated by $$\int_{window} \|\tilde{r}(t)\|^2 e^{-i\omega_0 t(\bar{\epsilon} - \epsilon)} dt \approx$$ [Eqn 7]

$$\int_{window} \|\tilde{r}(t)\|^2 dt - i \int_{window} \|\tilde{r}(t)\|^2 \omega_0 t(\bar{\epsilon} - \epsilon) dt.$$

We define $$R_0 = \int_{window} \|\tilde{r}(t)\|^2 t \, dt.$$ [Eqn 8]

Then we can write the imaginary part of the complex cross correlation as $$Im\{\int_{window} \tilde{r}(t) \tilde{u}^*(t) dt\} = (\epsilon - \bar{\epsilon}) \omega_0 R_0$$ [Eqn 9], where "*" denotes the complex conjugate. Rearranging this equation gives us $$\Delta \epsilon =$$ [Eqn 10], $$(\epsilon - \bar{\epsilon}) = \frac{Im\{\int_{window} \tilde{r}(t) \tilde{u}^*(t) dt\}}{\omega_0 R_0} = \frac{Im\{\int_{window} \tilde{r}(t) \tilde{u}^*(t) dt\}}{SF},$$

where SF is a slope factor.

The slope factor, SF, was derived above using some approximations. Writing the SF as derived above, referred to here as a single set data method, it is $$SF = \omega_0 R_0 = \omega_0 \int_{window} \|\tilde{r}(t)\|^2 t \, dt.$$ [Eqn 11]

The advantage of this form of the SF is that it uses only the envelope of the unstressed signal. This means that it can be calculated once and used for all iterations on that window. This improves the speed of the estimation and makes it more suitable for real-time implementations. Using a more complicated expression and a slightly different approximation one can identify a different expression for the SF. This different form will be referred to as the direct method herein, and it makes use of the envelopes of the complex ultrasound data. This form of the SF can be calculated as:

$$SF = \omega_0 \cdot \int_0^T t \cdot |\tilde{r}(t)| \cdot |\tilde{s}^*(t)| dt,$$ [Eqn. 12]

where $\omega_0$ is the center frequency of the ultrasound signals and | . . . | stands for taking the absolute value. It is interesting to note that the envelopes of the signals are changed only slightly by the applied stress, as opposed to the phase of the signals, which change a great deal. An examination of the equations above shows that Eqn. 12 reduces to Eqn. 11 when the envelopes of the two signals are the same.

Another way to calculate SF, identified as an adaptive method herein, can be used when the complex correlation function is calculated for a well defined amount of stretching, $\epsilon_0$. In this method, $\epsilon_0$ is applied to the unstressed ultrasound data r(t), and the imaginary part of the complex correlation function is calculated afterwards. The adaptive method is:

$$SF = \frac{\Im\left\{\int_0^T \tilde{r}(t) \cdot \tilde{r}^*(t(1-\epsilon_0)) dt\right\}}{\epsilon_0}.$$ [Eqn. 13]

The methods described above for calculating the SF are not meant to be limiting and it is envisioned that other comparable methods can be used. Regardless of the exact method employed to calculate the SF, once calculated, the SF is then used to estimate the strain in Eqn 10. Equation 10 gives an expression that can be used to calculate the actual strain 36 given an estimated strain, the imaginary part of the complex cross correlation 32, and the scale factor 34. This expression can be used to guide our iterative search and allow it to converge quickly; however, it is also envisioned that the expression can also be used without iteration, as it is approximately correct.

Within each correlation window, the strain estimation algorithm can be iterated as follows. First, the windows of data from the pre-stress and post-stress data sets are determined as described earlier. An initial estimate of the strain, $\epsilon_k$, is required to seed the algorithm. For the first window this estimate is either zero, or some other value that was determined through a different estimation process. The window of data from the post-stress data, s(t), is re-interpolated 30 such that it is stretched (or compressed) by the amount required to remove the estimated strain. (i.e., a re-stressed/re-stretched data set, $s(t/(1-\epsilon_k)+t_p)$ is calculated) The interpolation can take many forms including linear and higher order interpolations, fourier based interpolation, spline interpolation, or some other method.

Once the estimated strain has been "removed", and the SF 34 and the imaginary part of the complex correlation function 32 have been calculated, the updated strain estimate is calculated 36 using Eqn. 10. The strain for the next iteration ($\epsilon_{k+1}$) can then be determined using $$\epsilon_{k+1} = \epsilon_k + \Delta\epsilon$$ [Eqn. 14], where $\epsilon_k$ is the initial estimated strain of the current iteration and $\Delta\epsilon$ is value calculated in Eqn 10.

The technique then determines 38 whether additional iterations are needed to further minimize the imaginary part of the complex correlation function. That is, if a pre-determined number of iterations has not yet been performed 40, then technique increases 42 the value of parameter, k, by one and returns to 30. An additional iteration is then performed 30-36 as described above. If the pre-determined number of iterations has been performed 44 or some other criteria for completion has been met, the iteration loop is closed 46 for the current correlation window. While any number of iterations may be performed, it has been found that two iterations are often sufficient to estimate the local strain, $\epsilon$, for each correlation window.

For each line in a strain image, the iterative algorithm just described is applied on a window by window basis and the strain is estimated for each window. The algorithm begins with data nearest the ultrasound transducer (i.e., earliest in time). In the pre-stressed data, r(t), the windows are moved with a well defined spacing. For instance, the beginning of the window could be moved N samples and the length of window held constant. Here N is an arbitrary step size that will in part determine the resolution of the resulting strain image. The windows in the stressed data, s(t), are not moved in a regular pattern, but instead are positioned depending on the strain from previous windows in the line. The offset between the start of the window in the pre-stress data and the start of window in the post stressed data is called the pre-delay.

For ease of explanation, the calculation of a single line of strain data is here considered. The transducer is placed on the tissue or sample and a line of data is recorded. The transducer is pushed some amount and a second line of data is recorded with the tissue in a stressed state. In practice the transducer can be moving in and out, pushing and releasing the tissue and any two sets of data can be taken. Now, we have one line of pre-stressed data, r(t), for which the analytic or baseband signal can be calculated. There is also a second line of data that is stressed, s(t), and for which the analytic or baseband signal for this line can be calculated. It is assumed herein that the lines of data are from the same elevation and azimuthal locations and that only axial translation has been caused by the transducer motion, but the method is not limited to this. There are thus two lines of data, pre- and post-stress. The data close to the transducer face is well aligned because the transducer moved with the outer layer of tissue. For this reason it is assumed that there is no pre-delay. One window of data is taken from the pre-stress data and the same window of data from the post-stress data is also taken. The iterative strain algorithm is used to estimate the strain for those windows. The initial estimated strain which is required to start the iterative search for this window is assumed to be zero. This is a reasonable assumption since it is data near the face of the transducer and therefore has a small amount of strain. The calculated strain which is the result of the iterative algorithm is used both as the input estimate for the next window and to adjust the window location in the stressed data. A new window on the pre-stressed data is chosen by moving the window some fixed amount. A new window for the post-stressed data is chosen by adding a pre-delay to the fixed amount moved in the pre-stressed data. This pre-delay is a function of the previous strain values. That is, upon closing of the iterative loop for the current correlation window, the technique calculates 48 the pre-delay for a subsequent correlation window by applying the initial estimated strain, $\epsilon_{k+1}$. Thus, $$t_{p+1} = t_p + T_T \frac{\epsilon_{k+1}}{1 - \epsilon_{k+1}}, \quad [\text{Eqn. 15}]$$

wherein $T_\tau|$ is the time interval between two successive correlation windows. The new windows are used to estimate additional strain values. After each strain estimate, the windows are moved with the post-stress data window being adjusted by the updated pre-delay. This is repeated until the line is complete.

Referring again to FIG. 2, the technique next determines 50 whether there is any next correlation window for which to estimate the local strain. If there is a next correlation window for which to estimate strain 52, the calculated pre-delay is then applied 54 to the ultrasound data for the subsequent correlation window. That is, the technique returns to 30 and the calculated pre-delay is applied to the stressed ultrasound data set, s(t), and the local strain is determined for this subsequent correlation window. If there is no further correlation window 56, then the technique is ended 58 and the direct strain estimation technique 26 is terminated.

The analysis above was done for analytic signals. If proper care is taken to account for phase changes in the stretching of signals, the algorithm can be easily extended to baseband data. In fact the sampling rate requirements for good interpolation results are lower for baseband data than for analytic data. For this reason baseband data is more advantageous to real-time implementations. Additionally, the use of the imaginary part of the complex correlation function in the direct strain estimation technique 26 of the present invention allows for the application of direct strain estimation to broadband data, as opposed to existing techniques that are limited in application to narrowband data. Because the present invention takes advantage of the proportionality between the strain and the imaginary part of the complex correlation function, the need for an arctan function is eliminated. Thus, the efficiency with which the strain estimation can be carried out is greatly increased, and the elastography is made real-time capable.

The direct strain estimation technique 26 of the present invention improves the accuracy of the estimated strain and reduces the standard deviation thereof over known techniques. Strain noise level in known techniques is higher than that of the direct strain estimation technique 26 and increases further as the strain value increases. The direct strain estimation technique 26 of the present invention maintains constant noise levels when determining strain despite any increases in the strain value.

Beyond the actual direct estimation of the strain, the present invention also envisions a technique to: incorporate thresholds to filter out bad strain estimates, prospectively identify incorrect strain estimates before processing, and normalize strain data to reduce the biasing effect of incorrect strain estimates. These capabilities further improve the performance of the direct strain estimation technique described above.

It is known that for a particular strain algorithm there is an optimal strain level for which the elastographic signal-to-noise ratio is best. The signal-to-noise ratio is low for very low strains because the signal itself is small. For large strains, de-correlation prevents proper estimation and so the signal-to-noise is low because the noise is high for these large strain values. For the direct strain estimators we can apply this concept of an ideal strain at a finer scale. That is, a range of "good" strains can be defined by applying thresholds within which the estimated strain values should fall. If the estimated strain is less than a lower threshold, that estimate is considered to be suspect because it is likely to be noisy. Likewise, if the strain is greater than an upper threshold, it is also considered suspect because it is also likely to be noisy. As it turns out however, the local strain variation is usually not so much that estimates will vary in and out of the "good" range from window to window.

In addition to the signal-to-noise characteristics, there is another reason such a threshold may be helpful. If an estimate is wildly wrong, it is likely to be outside of the good range of strains. Hall et al (U.S. Pat. No. 6,508,768 B1) points out that there are also some physical limits on the strains based on an assumed geometry and imaging protocol. That is, some common sense limits on the strain can be determined and also used to set thresholds.

The question of what to do in the case of "suspect" strain estimates does not have a straight forward answer. The strain estimate is used for displaying the strain or a function of the strain in an image, and so eliminating erroneous values is important for display. Perhaps more importantly, the strain is also used to calculate the location for the next correlation window of data. If the next correlation window is only slightly misaligned from the previous window, the strain estimation algorithm will slowly recover over a few windows. If, however, the adjacent correlation windows are grossly misaligned, the algorithm will not recover. Thus, for large strain estimates which are most likely incorrect, it is preferred to simply zero this value or use a previous or interpolated value for purposes of window alignment. In effect, this means that the next correlation window will be off by some amount but may soon recover. Without such zeroing, a largely incorrect strain estimate could fatally misalign the next correlation window and not allow for the strain estimation algorithm to recover and correct for the mistaken strain estimate.

In addition to the level of strain, most direct strain algorithms calculate a quality coefficient that can be used as a measure of quality for the strain estimate. This quality coefficient can be a function of strain level, correlation value, location, and strain derivative. In a preferred embodiment, is used as a measure of quality for the strain estimate. Given two windows of data the normalized cross-correlation is calculated as:

$$\frac{\sum s_1 s_2^*}{\sqrt{\sum |s_1|^2 \sum |s_2|^2}}, \quad \text{[Eqn. 16]}$$

where $s_1$ and $s_2$ are the two signals being compared, * indicates complex conjugation, and the summations are over the length of the correlation window.

The cross correlation value is defined as a complex number. The phase of the complex cross correlation is related to the delay between the ultrasound signals and, in fact, this property is exploited by many of the displacement based strain algorithms to calculate the shift between signals. For the direct strain estimation algorithm, the phase should be zero after the signals are appropriately stretched or compressed. A large phase term indicates an error, and thresholds on the "residual phase" can be used to detect erroneous estimates. The real part of the complex cross correlation (often referred to as the correlation coefficient) is a measure of how well the signals match, including the shape of the signals and not just the shift between them. The value of this normalized version can range from −1 to +1. The sign of the correlation coefficient is related to the phase of the complex correlation and thus is another indicator of correlation window alignment. For an estimate of the strain to be valid, the resulting magnitude of the correlation coefficient should be very high. For phantom data, it is envisioned that the correlation coefficient is normally greater than 0.95 for good estimates. In practice, it is difficult to get such high correlation in real tissue data, and thus, thresholds are usually set much lower. Therefore, as applied to direct strain estimation, if the correlation coefficient measured is less than some selected threshold, the measured strain value is treated as suspect.

The correlation coefficient threshold can be a simple constant or it can vary with tissue depth. That is, one might have a higher threshold near the surface of the ultrasound transducer and an increasingly less strict threshold as you move away from the transducer. Also, the threshold can be a function of previous estimated strain values. For instance, if the difference between the current strain estimate and the previous strain estimate is greater than some threshold (and the previous estimate had a high correlation or is believed to be reliable), then the threshold on the current correlation value can be adjusted such that it is more strict for values which are very different from the past or average past values.

For a strain estimate with correlation coefficient below a threshold, it is possible that the poor result is caused by applying the wrong pre-delay to the post-stress data. The pre-delay may be corrected by the correlation coefficient. The correction is composed of two steps. First, assuming strain is small enough, the pre-delay is corrected using the phase of the correlation coefficient. However, it is possible that the phase is wrapped. A second step is necessary to unwrap the phase. The phase unwrapping is accomplished in a try-and-error fashion. The pre-delay is first shifted left by one period of the center frequency and the cross correlation is calculated. If the new correlation is better, the pre-delay is further shifted left by one period and the correlation is compared again; otherwise, the pre-delay is shifted right by two periods to compare the correlation. The search goes on till a predefined region is covered and the best-correlated pre-delay will be kept as the new pre-delay.

Beyond these restrictions on the correlation coefficient, one can also place a threshold on the derivatives of the strain. The estimated strain is expected to vary smoothly for most tissue. If, however, a current strain value is very different from the previous value, or an average of some number of previous values, then it may be incorrect. A threshold on this difference between a current estimated strain and previous estimated strain(s) can be used to avoid these large errors.

More generally, one can also calculate a quality coefficient for the particular strain value in question. This quality coefficient may be some function of the strain level, the expected average strain, the average strain, the correlation value, the location in the image, the difference from spatially close values, the difference from temporally close values, or numerous other parameters. The above mentioned threshold concepts are specific versions of this more generic quality coefficient. A well designed quality coefficient has natural ranges and thus allows for an intuitive setting of a threshold. All thresholds can be set by experimentally determining performance for some range of thresholds and choosing the best option.

Beyond the various thresholds set forth above, additional filtering can also be employed to further improve the performance of the direct strain estimator. This filtering can be done either spatially, or temporally, or both. The filtering is done not simply to improve the smoothness of the displayed image, but also to prevent errors in the strain estimation itself. As described above, any error in the strain estimation also generates an error in the correlation window location for the next strain estimate. To further minimize such occurrences, the strain estimates can be filtered over beams in each window location to provide a smooth estimate of the strain. These filtered values of the strain can be used to adjust the window location for the next strain estimate. Even by applying such a filtering process, small phase shift errors in the next correlation window can still occur. Thus, the filtered strain values are used only if the actual strain value differs from the filtered value by some threshold value. That is, is the difference between an estimated strain value and a filtered estimated strain value exceeds a certain threshold, the filtered strain value can replace the original estimated strain value. Such use of a filtered strain value can more effectively prevent errors in the next correlation window than a simple zeroing or clipping of the estimated strain. However, it is envisioned that such zeroing or clipping of the estimated strain could be used in the present invention.

In an initial strain estimation pass, all strain estimates with correlations below a threshold are excluded from the window delay calculations (i.e., made zero for the purposes of window selection). After a complete line of data is processed, the iterative direct strain estimation algorithm goes back and finds places where the correlation dipped down and then returned to a fairly high value. For each of these dips the strain algorithm is run backwards starting from the strain value with high correlation and ending at the point where the correlation had originally become low. Thus, the strain estimate at each window may be obtained by retrospective processing using the same abovementioned algorithm, but with initial strain estimate and pre-delay that are derived from the pre-delay and strain values one window after the current correlation window. As a result, the strain value will be updated if the correlation coefficient is higher than the one in the initial pass.

To further improve the direct strain estimation technique 26, a preprocessing step can be employed to identify regions in a B-mode image for which strain estimates are likely to be incorrect. That is, dark regions in the B-mode image caused by a blood vessel or anechoic cyst often cause problems for strain estimation, as the signal from these regions is small and, thus, the elastographic signal-to-noise is also small. It is in these dark regions of the image that strain estimates can be grossly incorrect. As described above, such incorrect estimates will misplace subsequent correlation windows and the strain estimation for those windows. If these dark regions in the B-mode image are identified prior to strain estimation, they can be properly accounted for.

For such a preprocessing method, strain estimation would occur as normal in each correlation window until a dark region in the B-mode image is reached. Upon reaching such a dark region, an estimated strain value would be set to zero or thresholds made more stringent. Once out of the dark region, correlation windows would be resynchronized based on the estimated strain data before the dark region and a strain for that dark region. Such resynchronization is done with a more advanced and computationally intensive search guided by an initial guess of the estimated strain in the dark region based on the average strain prior to the dark region. This search could be correlation based to find the best match between the correlation window prior to the dark region window from the dark region window itself. To improve correlation, the dark region window could be pre-compressed or stretched before the search. Once the post dark region window location is found, the direct strain algorithm can continue as normal.

As described above, direct strain estimators try to determine the strain for a particular window of data. This is usually done using a cross correlation based algorithm. If a particular data point in the window has a large amplitude, it will be more heavily weighted in the cross correlation and the strain value can be biased by this weighting. The strain estimate is a measure of how much the window has been compressed or stretched, and is very sensitive to the phase and frequency of a local ultrasound signal, but is not so sensitive to the amplitude of the local signals. By normalizing the ultrasound data so that the phase information is preserved but the magnitude is made to be nearly uniform, the bias introduced by the large amplitude reflectors can be reduced. This bias is often seen as banding in the strain images with the band size corresponding to the window length.

A broadband signal can be expressed as $$s(t)=A(t)e^{i(\omega_0 t+\phi(t))} \quad [\text{Eqn. 17}],$$

where s(t) is the signal, A(t) is a time varying amplitude function, $\omega_0$ is the center angular frequency, and $\phi(t)$ is a phase, which can be assumed to be a constant over the window processing length. The signal is normalized by simply dividing out A(t), $$f(t)=s(t)/A(t)=e^{(i\omega_0 t+\phi(t))} \quad [\text{Eqn. 18}],$$

but there are complications that need to be considered with this normalization. When A(t) is small or zero, the function approached infinity. When there is a noise term added to the signal it is difficult to calculate the true A(t). So in practice, A(t) is calculated as the magnitude of s(t)+n(t), where n(t) is an unknown noise. The estimate of A(t) is then clipped for values of A(t) less than a set threshold, wherein A(t) is scaled so that the clipped values are in unity. A(t) is then filtered to get a smoothed version and to remove some of the noise. The signal, s(t) is then divided by this clipped, scaled, and filtered version of A(t). This results in a signal which has approximately uniform magnitude and has phase and zero crossings which are virtually identical to the original signal. This normalized data is then used for the strain estimation.

Therefore, in accordance with one embodiment of the present invention, an ultrasound system includes an ultrasound device configured to acquire a pair of ultrasound data sets from a biological tissue, wherein the pair of ultrasound data sets comprising acquired ultrasound data of the biological tissue in a relaxed state and in a tensed state. The system further includes a computer programmed to re-stretch the tensed state ultrasound data set, calculate an imaginary part of a complex correlation function between the relaxed state ultrasound data set and the re-stretched tensed state ultrasound data set, calculate a slope factor, and estimate a strain of the biological tissue from a relationship between the calculated imaginary part and the slope factor.

In accordance with another embodiment of the present invention, a method of determining strain in an elastic tissue includes the steps of accessing a first set of ultrasound data acquired from the elastic tissue in an unstressed state and accessing a second set of ultrasound data acquired from the elastic tissue in a stressed state. The method further includes the steps of estimating a local strain of the elastic tissue based on an imaginary part of a complex correlation function between the first and second data sets and calculating a pre-delay for a subsequent correlation window based on the estimated local strain.

In accordance with yet another embodiment of the present invention, a computer readable storage medium includes a computer program to adaptively control an ultrasound system for measuring strain in elastic tissue, the computer program representing a set of instructions that when executed by a computer causes the computer to analyze ultrasound data acquired from the elastic tissue between a stressed state and an unstressed state and estimate a local strain of the elastic tissue by performing an iterative calculation, wherein the local strain is proportional to an imaginary part of a complex correlation function of the acquired ultrasound data between the stressed state and the unstressed state. The computer program further causes the computer to calculate a pre-delay for a subsequent correlation window based on the estimated local strain.

The present invention has been described in terms of the preferred embodiment, and it is recognized that equivalents, alternatives, and modifications, aside from those expressly stated, are possible and within the scope of the appending claims.

What is claimed is:

1. An ultrasound system comprising:
    an ultrasound device configured to acquire a pair of ultrasound data sets from a biological tissue, the pair of ultrasound data sets comprising acquired ultrasound data of the biological tissue in a relaxed state and in a tensed state, respectively;
    a computer programmed to:
        (a) stretch the tensed state ultrasound data set;
        (b) calculate an imaginary part of a complex correlation function between the relaxed state ultrasound data set and the stretched tensed state ultrasound data set;
        (c) calculate a slope factor (SF) using one of a single set data method, a direct method, and an adaptive method, wherein:
        the single set data method is $$SF = \omega_0 R_0 = \omega_0 \int_{window} \|\tilde{r}(t)\|^2 t \, dt;$$

the direct method is $SF = \omega_0 \cdot \int_0^T t \cdot |\tilde{r}(t)| \cdot |\tilde{s}^*(t)| dt$; and
the adaptive method is $$SF = \frac{\Im\left\{\int_0^T \tilde{r}(t) \cdot \tilde{r}^*(t(1-\varepsilon_0)) \, dt\right\}}{\varepsilon_0},$$

wherein:
    $\omega_0$ corresponds to the center frequency of the relaxed state ultrasound data, $$R_0 = \int_{window} \|\tilde{r}(t)\|^2 t \, dt,$$

T corresponds to a length of a correlation window used for strain estimation,
$\tilde{r}(t)$ corresponds to an analytic signal version of the relaxed state ultrasound data,
$\tilde{s}(t)$ corresponds to an analytic signal version of the tensed state ultrasound data,
$\tilde{r}^*$ corresponds to a complex conjugate of the relaxed state ultrasound data,
$\tilde{s}^*$ corresponds to a complex conjugate of the tensed state ultrasound data,
$\varepsilon_0$ corresponds to a defined amount of stretching applied to the relaxed state ultrasound data; and
        (d) estimate a strain of the biological tissue from a relationship between the calculated imaginary part and the slope factor.

2. The ultrasound system of claim 1 wherein the computer is further programmed to perform functions (a)-(d) for a pre-determined number of iterations to minimize the imaginary part of the complex correlation function.

3. The ultrasound system of claim 1 wherein the computer is further programmed to calculate a pre-delay for a subsequent correlation window based on the estimated strain.

4. The ultrasound system of claim 3 wherein the computer is further programmed to:
    apply the pre-delay to the subsequent correlation window; and
    perform functions (a)-(d) for the subsequent correlation window.

5. The ultrasound system of claim 3 wherein the computer is further programmed to perform an initialization, and wherein performing the initialization further comprises:
    setting the pre-delay to a value of zero;
    setting an initial estimated strain to a value of zero; and
    performing functions (a)-(d) in a first iteration for the pre-delay having the value of zero and the initial estimated strain having the value of zero.

6. The ultrasound system of claim 1 wherein the computer is further programmed to adjust a pre-delay based on a correlation coefficient.

7. The ultrasound system of claim 4 wherein the computer is further programmed to calculate the stretched tensed state ultrasound data set by applying the pre-delay and the estimated strain to the tensed state ultrasound data set.

8. The ultrasound system of claim 1 wherein the computer is further programmed to:
    set a minimum strain threshold and a maximum strain threshold for the estimated strain; and
    perform one of a clipping function, a zeroing function, and an interpolating function on the estimated strain for estimated strains above the maximum strain threshold and below the minimum strain threshold.

9. The ultrasound system of claim 1 wherein the computer is further programmed to:
    set a correlation window threshold for a change in the estimated strain from a current correlation window to a subsequent correlation window; and
    perform one of a clipping function, a zeroing function, and an interpolating function on the estimated strain if the change in the estimated strain exceeds the correlation window threshold.

10. The ultrasound system of claim 1 wherein the computer is further programmed to:
    set a quality coefficient threshold on a quality coefficient; and
    perform one of a clipping function, a zeroing function, and an interpolating function on the estimated strain if the quality coefficient is below the quality coefficient threshold, wherein the quality coefficient is one of a correlation value, strain value, location, and strain derivative.

11. The ultrasound system of claim 1 wherein the computer is further programmed to:
    filter the estimated strain by at least one of a spatial filtering and a temporal filtering; and
    replace the estimated strain with the filtered estimated strain.

12. The ultrasound system of claim 11 wherein the computer is further programmed to weight the filtered estimated strain by a correlation coefficient.

13. The ultrasound system of claim 11 wherein the computer is further programmed to:
    set a filtering threshold for a difference between the estimated strain and the filtered estimated strain; and replace the estimated strain with the filtered estimated strain if the difference between the estimated strain and the filtered estimated strain exceeds the filtering threshold.

14. The ultrasound system of claim 1 wherein the computer is further programmed to retrospectively process the estimated strain to obtain an updated estimated strain based on an initial strain estimate and a pre-delay from a subsequent correlation window.

15. The ultrasound system of claim 1 wherein the computer is further programmed to:
prospectively identify low signal regions in a B-mode image; and
set the estimated strain to a value of zero for the low signal regions.

16. The ultrasound system of claim 1 wherein the computer is further programmed to normalize the relaxed state ultrasound data set and the tensed state ultrasound data set to reduce effect of an amplitude of an ultrasound signal on the estimated strain.

17. A method of determining strain in an elastic tissue comprising:
a) accessing a first set of ultrasound data acquired from the elastic tissue in an unstressed state;
b) accessing a second set of ultrasound data acquired from the elastic tissue in a stressed state;
c) applying a pre-delay and an initial estimated strain to the stressed ultrasound data signal to obtain a re-stressed ultrasound data signal;
d) calculating an imaginary part of a complex correlation function between the unstressed ultrasound data signal and the re-stressed ultrasound data signal;
e) calculating a slope factor using one of a single set data method, a direct method, and an adaptive method, wherein:
the single set data method is $$SF = \omega_0 R_0 = \omega_0 \int_{window} \|\tilde{r}(t)\|^2 t\, dt;$$

the direct method is $$SF = \omega_0 \cdot \int_0^T t \cdot |\tilde{r}(t)| \cdot |\tilde{s}^*(t)|\, dt; \text{ and}$$

the adaptive method is $$SF = \frac{\Im\left\{\int_0^T \tilde{r}(t) \cdot \tilde{r}^*(t(1-\varepsilon_0))\, dt\right\}}{\varepsilon_0},$$

wherein:
$\omega_0$ corresponds to the center frequency of the relaxed state ultrasound data, $$R_0 = \int_{window} \|\tilde{r}(t)\|^2 t\, dt,$$

T corresponds to a length of a correlation window used for strain estimation, $\tilde{r}(t)$ corresponds to an analytic signal version of the relaxed state ultrasound data,
$\tilde{s}(t)$ corresponds to an analytic signal version of the tensed state ultrasound data,
$\tilde{r}^*$ corresponds to a complex conjugate of the relaxed state ultrasound data,
$\tilde{s}^*$ corresponds to a complex conjugate of the tensed state ultrasound data,
$\varepsilon_0$ corresponds to a defined amount of stretching applied to the relaxed state ultrasound data;
f) estimating a local strain of the elastic tissue based on the imaginary part of the complex correlation function and the slope factor;
g) repeating steps (c)-(f) for a pre-determined number of iterations; and
h) calculating a pre-delay for a subsequent correlation window based on the estimated local strain.

18. The method of claim 17 further comprising performing an initialization for the correlation window, wherein performing the initialization further comprises:
setting the pre-delay to a value of zero;
setting the initial estimated strain to a value of zero; and
performing functions (c)-(f) in a first iteration for the pre-delay having the value of zero and the initial estimated strain having the value of zero.

19. The method of claim 17 wherein the repeating of steps (c)-(f) for a pre-determined number of iterations minimizes the imaginary part of the complex correlation function.

20. The method of claim 17 further comprising:
setting at least one of a strain threshold on the estimated strain, a correlation window threshold for a change in the estimated strain from a current correlation window to the subsequent correlation window, and a correlation coefficient threshold on a correlation coefficient; and
performing one of a clipping function, a zeroing function, and an interpolating function on the estimated strain if the at least one of the strain threshold, the correlation window threshold, and the correlation coefficient threshold is crossed.

21. The method of claim 17 further comprising:
filtering the estimated strain based on at least one of a spatial filter and a temporal filter;
setting a filtering threshold for a difference between the estimated strain and the filtered estimated strain;
replacing the estimated strain with the filtered estimated strain if the difference between the estimated strain and the filtered estimated strain exceeds the filtering threshold; and
if the estimated strain is replaced with the filtered estimated strain, weighting the filtered estimated strain by a correlation value.

22. The method of claim 17 further comprising the step of retrospectively processing the estimated strain to obtain an updated estimated strain based on an initial strain estimate and a pre-delay from a subsequent correlation window.

23. The method of claim 17 further comprising the steps of:
prospectively identifying low signal regions in a B-mode image; and
setting the estimated strain to a value of zero for the low signal regions.

24. A non-transient computer readable storage medium having a computer program to adaptively control an ultrasound system for measuring strain in elastic tissue, the computer program representing a set of instructions that when executed by a computer causes the computer to:
a) analyze ultrasound data acquired from the elastic tissue between a stressed state and an unstressed state;

b) apply a pre-delay and an initial estimated strain to the stressed state ultrasound data to obtain re-stressed state ultrasound data;
c) calculate an imaginary part of a complex correlation function between the unstressed state ultrasound data and the re-stressed state ultrasound data;
d) calculate a slope factor using one of a single set data method, a direct method, and an adaptive method, wherein:
the single set data method is $$SF = \omega_0 R_0 = \omega_0 \int_{window} \|\tilde{r}(t)\|^2 t\, dt;$$

the direct method is $$SF = \omega_0 \cdot \int_0^T t \cdot |\tilde{r}(t)| \cdot |\tilde{s}^*(t)|\, dt; \text{ and}$$

the adaptive method is $$SF = \frac{\Im\left\{\int_0^T \tilde{r}(t) \cdot \tilde{r}^*(t(1-\varepsilon_0))\, dt\right\}}{\varepsilon_0},$$

wherein:
$\omega_0$ corresponds to the center frequency of the relaxed state ultrasound data, $$R_0 = \int_{window} \|\tilde{r}(t)\|^2 t\, dt,$$

T corresponds to a length of a correlation window used for strain estimation,
$\tilde{r}(t)$ corresponds to an analytic signal version of the relaxed state ultrasound data,
$\tilde{s}(t)$ corresponds to an analytic signal version of the tensed state ultrasound data,
$\tilde{r}^*$ corresponds to a complex conjugate of the relaxed state ultrasound data,
$\tilde{s}^*$ corresponds to a complex conjugate of the tensed state ultrasound data,
$\epsilon_0$ corresponds to a defined amount of stretching applied to the relaxed state ultrasound data;
e) estimate the local strain based on the imaginary part of a complex correlation function of the acquired ultrasound data between the stressed state and the unstressed state and the slope factor;
f) repeat steps (b)-(e) for a pre-determined number of iterations; and
g) calculate a pre-delay for a subsequent correlation window based on the estimated local strain.

25. The non-transient computer readable storage medium of claim 24 wherein the set of instructions further causes the computer to:
set at least one of a strain threshold, a correlation window threshold, and a correlation coefficient threshold on the estimated strain; and
perform one of a clipping function, a zeroing function, and an interpolating function on the estimated strain if the at least one of the strain threshold, the correlation window threshold, and the correlation coefficient threshold is crossed.

26. The non-transient computer readable storage medium of claim 24 wherein the set of instructions further causes the computer to:
filter the estimated strain by at least one of a spatial filtering and a temporal filtering;
set a filtering threshold for a difference between the estimated strain and the filtered estimated strain; and
replace the estimated strain with the filtered estimated strain if the difference between the estimated strain and the filtered estimated strain exceeds the filtering threshold.

27. The non-transient computer readable storage medium of claim 26 wherein the set of instructions further causes the computer to weight the filtered estimated strain by a correlation coefficient.

* * * * *